United States Patent [19]

Dingwall et al.

[11] 4,335,057
[45] Jun. 15, 1982

[54] 4-(2',2,2'-TRIHALOGENOETHYL)-CYCLOBUTANE-1-SULFONIC ACID SALTS WITH OPTICALLY ACTIVE BASES

[75] Inventors: John G. Dingwall, Sale, England; Hans Greuter, Cos Cob, Conn.; Pierre Martin, Rheinfelden, Switzerland; Peter Ackermann, Reinach, Switzerland; Laurenz Gsell, Basel, Switzerland

[73] Assignee: Ciba-Geigy Corporation, Ardsley, N.Y.

[21] Appl. No.: 219,803

[22] Filed: Dec. 24, 1980

Related U.S. Application Data

[62] Division of Ser. No. 103,983, Dec. 17, 1979, Pat. No. 4,299,967.

[30] Foreign Application Priority Data

Dec. 15, 1978 [CH] Switzerland ............... 12784/73

[51] Int. Cl.$^3$ ............................................. C07C 143/20
[52] U.S. Cl. ............................ 260/501.19; 260/456 R; 260/456 P; 260/503; 546/35; 546/53; 546/134; 546/282
[58] Field of Search ............. 260/456 R, 503, 501.19, 260/501.21, 456 P; 546/35, 134, 53, 282

[56] References Cited

U.S. PATENT DOCUMENTS 4,255,351  3/1981  Martin et al. ............... 260/456 R

*Primary Examiner*—Nicky Chan
*Attorney, Agent, or Firm*—Frederick H. Rabin

[57] ABSTRACT

There is described a new process for the preparation of optically active 2-(2',2'-dihalogenovinyl)-cyclopropane-1-carboxylic acids substituted in the 3 position, and derivatives thereof. A racemate of certain cyclobutanones is reacted with a sulfurous acid salt of an optically active base to obtain a mixture of diastereomeric 4-(2',2',2'-trihalogenoethyl)-cyclobutane-2-sulfonic acid salts; this mixture is then separated into the pure diastereomeric sulfonic acid salts. Either the pure diastereomeric sulfonic acid salts are converted directly to the desired optically active products, or the optically active cyclobutanones obtained from the pure diastereomeric sulfonic acids salts by decomposition are converted, in the presence of a base, to the desired product. Optionally, the product, optically active 2-(2',2'-dihalogenovinyl)-cyclopropane-2-carboxylic acids can be converted to their 1',2'-dibromo derivatives.

3 Claims, No Drawings

4-(2',2',2'-TRIHALOGENOETHYL)-CYCLOBUTANE-1-SULFONIC ACID SALTS WITH OPTICALLY ACTIVE BASES

This is a division of application Ser. No. 103,983, filed on Dec. 17, 1979, now U.S. Pat. No. 4,299,967.

The present invention relates to a novel process for the preparation of optically active 2-(2',2'-dihalogenovinyl)-cyclopropane-1-carboxylic acids substituted in the 3-position, and derivatives thereof, and also to novel 4-(2',2',2'-trihalogenoethyl)-cyclobutane-1-sulfonic acid salts. The said cyclopropanecarboxylic acids and their derivatives are valuable starting materials for the preparation of agents for pest control, especially insecticides, or can be employed direct as agents for pest control.

It is generally known that in the case of biologically active chemical substances with an optically active centre, as a rule only one of the two possible mirror images is biologically active, but the other is inactive.

The known insecticidal pyrethroids are chemical substances which possess several such optically active centres. The literature [cf. M. Elliott: Synthetic Pyrethroids, ACS Symposium Series 42, Am. Chem. Soc. 2–9 (1977)] shows that in this case also the configuration at these centres is decisive in determining the insecticidal activity. Therefore, there is an urgent need for simple economical processes which enable pyrethroids to be synthesised with the optimum effective (insecticidal) configuration. The result of this is that only the biologically active components of a pyrethroid preparation are used. The amounts applied and the pollution of the environment are thus far lower than in the case of the use of pyrethroid preparations which also contain less active or entirely inactive isomers.

Various processes for the preparation of optically active 2-(2',2'-dihalogenovinyl)-3,3-dimethylcyclopropane-1-carboxylic acids have been disclosed in the literature, but these processes are not able to meet the above demands in all respects. Japanese Published Specifications Nos. 50-131,953, 51-36,441 and 51-143,647 disclose processes for resolving the racemates of trans-2-(2',2'-dichlorovinyl)-3,3-dimethyl-cyclopropanecarboxylic acid or mixtures of the trans- and cis-acids by reaction with specific optically active amines and decomposition of the resulting pure diastereomeric salts. Furthermore, it has been disclosed in German Offenlegungsschrift No. 2,628,477 that optically active 2-(2',2'-dichlorovinyl)-3,3-dimethyl-cyclopropanecarboxylic acids which have the undesired, that is to say biologically less active, configuration, especially the (−)-trans-isomer, can be racemised by exposure to UV light in the presence of photosensitisers. However, the yields of the desired racemate are low and, moreover, the proportion of trans-acid in this product is very predominant, so that this process is not suitable for the preparation of cis-acids, which for certain applications display a greater activity and are therefore particularly preferred.

According to British Pat. No. 1,446,304, optically active 2-(2',2'-dihalogenovinyl)-3,3-dimethyl-cyclopropanecarboxylic acids and their alkyl esters can also be prepared by the Wittig reaction, using optically active caronaldehyde derivatives as the starting materials. The optically active caronaldehyde derivatives required for this purpose are, however, accessible only with difficulty, in that they have to be prepared by ozonolysis, either from naturally occurring chrysanthemumic acid, which is not obtainable in any desired amount, or from synthetic chrysanthemumic acid. On racemisation of the acid or of derivatives thereof having the undesired configuration, high proportions of products with the trans-configuration are formed.

Finally, according to Japanese Published Specification No. 50-160,241, optically active cyclopropanecarboxylic acid esters can also be prepared by reacting suitable olefins with ethyl diazoacetate in the presence of optically active catalysts (carbene addition). However, the yields of optically active cyclopropanecarboxylic acid esters are unsatisfactory. Moreover, health risks and risks of accident are associated with the handling of the ethyl diazoacetate required for the reaction.

A process has now been found which enables optically active 2-(2',2'-dihalogenovinyl)-cyclopropanecarboxylic acids substituted in the 3-position, and derivatives thereof, to be rendered accessible, with high proportions of cis-isomers, in a simpler and more economical manner and avoiding the above disadvantages.

The invention thus relates to a process for the preparation of optically active cyclopropanecarboxylic acid derivatives of the formula I or I'

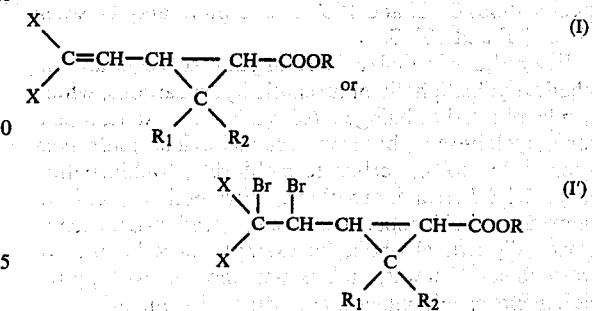

in which X is chlorine or bromine, one of the radicals $R_1$ and $R_2$ is methyl and the other is hydrogen or methyl, or $R_1$ and $R_2$ together are alkylene having 2–4 carbon atoms, and R is hydrogen, alkyl having 1–4 carbon atoms or a group (a)

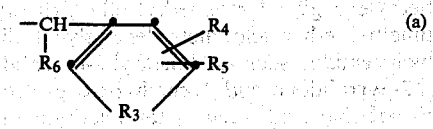

in which $R_3$ is oxygen, sulfur or 1,2-phenyl, $R_4$ is hydrogen, methyl, benzyl, phenoxy, 4-methylphenoxy, 4-chlorophenoxy, 4-fluorophenoxy or phenylmercapto, $R_5$ is hydrogen, fluorine, chlorine or methyl and $R_6$ is hydrogen, cyano or ethynyl; by converting a racemate of a cyclobutanone of the formula II

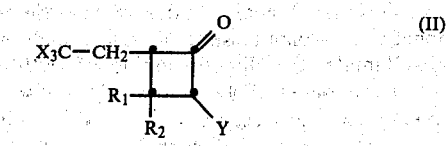

in which X, $R_1$ and $R_2$ are as defined under formula I and Y is chlorine, bromine or a group —$OSO_2R'$, in which R' is alkyl, halogenoalkyl, benzyl, naphthyl or substituted or unsubstituted phenyl, by reaction with a sulfurous acid salt of an optically active base A, to a mixture of diastereomeric sulfonic acid salts of the formula III

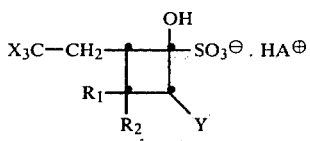

in which X, $R_1$, $R_2$ and Y are as defined and A is an optically active base, separating this mixture into the pure diastereomeric sulfonic acid salts of the formula III and converting either the pure diastereomeric sulfonic acid salts of the formula III direct, or the optically active cyclobutanones of the formula II obtained from the said salts by decomposition, in the presence of a base to an optically active cyclopropanecarboxylic acid derivative of the formula I and, if desired, converting the latter by bromination to an optically active cyclopropanecarboxylic acid derivative of the formula I'.

The reaction of the racemates of cyclobutanones of the formula II with a sulfurous acid salt of an optically active base A is advantageously carried out in the presence of an inert organic solvent at temperatures between about 0° C. and 100° C. and preferably between about 20° and 60° C.

Examples of suitable inert organic solvents are aliphatic, cycloaliphatic or aromatic hydrocarbons, which can be nitrated or halogenated, such as n-hexane, n-pentane, cyclohexane, benzene, toluene, xylenes, nitrobenzene, chloroform, carbon tetrachloride, trichloroethylene, 1,1,2,2-tetrachloroethane, nitromethane, chlorobenzene, dichlorobenzenes and trichlorobenzenes; lower aliphatic alcohols, for example those having not more than 6 C atoms, such as methanol, ethanol, propanol, isopropanol, butanols and pentanols; aliphatic diols, such as ethylene glycol and diethylene glycol; ethylene glycol monoalkyl and dialkyl ethers and diethylene glycol monoalkyl and dialkyl ethers, each having 1–4 C atoms in the alkyl moieties, such as ethylene glycol monomethyl ether, ethylene glycol monoethyl ether, ethylene glycol dimethyl ether and ethylene glycol diethyl ether, diethylene glycol monomethyl ether and diethylene glycol monoethyl ether, diethylene glycol dimethyl ether and diethylene glycol diethyl ether; cyclic amides, such as N-methyl-2-pyrrolidone, N-acetyl-2-pyrrolidone and N-methyl-ε-caprolactam; amides of carbonic acid, such as tetramethylurea and dimorpholinocarbonyl; amides of phosphorous acid, of phosphoric acid, of phenylphosphonic acid or of aliphatic phosphonic acids having 1–3 C atoms in the acid moiety, such as phosphoric acid triamide, phosphoric acid tris-(dimethylamide), phosphoric acid trimorpholide, phosphoric acid tripyrrolinide, phosphoric acid bis-(dimethylamide)-morpholide, phosphorous acid tris-(dimethylamide) and the tetramethyldiamide of methanephosphonic acid; amides of sulfuric acid or of aliphatic or aromatic sulfonic acids, such as tetramethylsulfamide, the dimethylamide of methanesulfonic acid or p-toluenesulfonic acid amide; sulfur-containing solvents, such as organic sulfones and sulfoxides, for example dimethylsulfoxide and sulfolane; aliphatic nitriles, especially alkylnitriles having 2–5 C atoms, such as acetonitrile, propionitrile and butyronitrile; 3-alkoxypropionitriles having 1 or 2 C atoms in the alkoxy moiety, such as 3-methoxypropionitrile and 3-ethoxypropionitrile; aromatic nitriles, in particular benzonitrile; alkyl esters and alkoxyalkyl esters of aliphatic monocarboxylic acids having a total of 2–6 C atoms, such as methyl formate and ethyl formate, methyl acetate, ethyl acetate, n-butyl acetate and isobutyl acetate; cyclic ethers, such as tetrahydrofuran, tetrahydropyran and dioxan; dialkyl ethers, each having 1–4 C atoms in the alkyl moieties, such as diethyl ether, di-n-propyl ether and di-isopropyl ether; and N,N-dialkylamides of aliphatic monocarboxylic acids having 1–3 C atoms in the acid moiety, such as N,N-dimethylformamide, N,N-dimethylacetamide, N,N-diethylacetamide and N,N-dimethylmethoxyacetamide.

Preferred solvents are polar solvents, in particular those which are miscible with water, such as aliphatic alcohols, aliphatic diols, ethylene glycol monoalkyl ethers and diethylene glycol monoalkyl ethers, cyclic amides, amides of phosphoric acid or of phosphorous acid, sulfoxides, alkylnitriles, cyclic ethers and N,N-dialkylamides of aliphatic monocarboxylic acids of the abovementioned type, especially methanol, ethanol, propanol, isopropanol, ethylene glycol and diethylene glycol, ethylene glycol monomethyl ether and ethylene glycol monoethyl ether, diethylene glycol monomethyl ether and diethylene glycol monoethyl ether, N-methyl-2-pyrrolidone, phosphoric acid tris-(dimethylamide), phosphorous acid tris-(dimethylamide), dimethylsulfoxide, acetonitrile, tetrahydrofuran, dioxan, N,N-dimethylformamide and N,N-dimethylacetamide.

Compounds which can be employed as optically active bases or sulfurous acid salts of an optically active base in the process according to the invention are compounds known per se, especially amines. Examples of suitable optically active bases are: S(+)-2-amino-1-butanol, R(−)-2-aminobutanol, L(+)-threo-2-amino-1-phenyl-1,3-propanediol, (−)-brucine, (+)-quinidine, (−)-quinine, (−)-cinchonidine, (+)-cinchonine, (+)-dehydroabietylamine, (+)-yohimbine, (−)-nicotine and further alkaloids with optically active centres, (−)-ephedrine, (+)-ephedrine, (−)-N-methyl-ephedrine, R(+)-1-naphthyl-1-ethylamine, S(−)-1-naphthyl-1-ethylamine, S(−)-1-phenylethylamine, R(+)-1-phenylethylamine, (+)-pseudoephedrine, (−)-α-phenyl-β-p-tolylethylamine and (−)- and (+)-threo-1-(p-nitrophenyl)-2-N,N-dimethylaminopropane-1,3-diol. It is also possible to use esters of aminoacids in the optically active form, such as the methyl ester of L-alanine, the ethyl ester of L-leucine, the tert.-butyl ester of L-phenylalanine, the methyl ester of L-methionine and the benzyl ester of L-valine, and also further derivatives of optically active aminoacids.

Compounds preferably used as the optically active base A are R(−)-2-amino-1-butanol, (−)-ephedrine, (+)-ephedrine, S(−)-1-phenylethylamine, R(+)-1-phenylethylamine or (+)-threo-1-(p-nitrophenyl)-2-N,N-dimethylaminopropane-1,3-diol or the sulfurous acid salts of these bases.

The optically active base A or the sulfurous acid salt of an optically active base A is advantageously employed in an amount of 0.5 to 1.5 mol equivalents, based on the racemic cyclobutanone of the formula II.

The sulfurous acid salt of the optically active base A can be employed as such or can be produced in situ. Preferably, the sulfurous acid salt of the optically active base A is produced in situ. For this purpose, the racemic cyclobutanone of the formula II and the optically active base A are dissolved in a water-containing solvent of the abovementioned type and sulfur dioxide is passed into the solution. Water and sulfur dioxide are used in an amount of at least one mol equivalent, based on the optically active base A.

The separation of mixtures of diastereomeric salts of the formula III can be carried out by methods known per se. As a rule, separation is effected by fractional crystallisation in a suitable inert organic solvent, especially in water-miscible organic solvents of the abovementioned type and in particular in aqueous methanol, ethanol, acetonitrile, tetrahydrofuran and dioxan.

The diastereomeric salts of the formula III are novel compounds and are likewise a subject of the invention.

Preferred compounds of the formula III are those in which A has the preferred meaning defined above, X is chlorine or bromine, one of $R_1$ and $R_2$ is methyl and the other is hydrogen or methyl, or $R_1$ and $R_2$ together are alkylene having 2-3 C atoms, especially ethylene, and Y is chlorine, bromine or a group $-OSO_2R'$, in which R' is alkyl or halogenoalkyl having 1-4 C atoms, benzyl, phenyl, methylphenyl, nitrophenyl, chlorophenyl or bromophenyl, and in particular compounds of the formula II and III in which A has the preferred meaning defined above and X is chlorine, $R_1$ and $R_2$ are each methyl and Y is a group $-OSO_2R'$, in which R' is methyl, 4-methylphenyl or 4-bromophenyl.

Particularly preferred compounds of the formula III are those in which A has the preferred meaning defined above, X and Y independently of one another are chlorine or bromine and one of $R_1$ and $R_2$ is methyl and the other is hydrogen or methyl, or $R_1$ and $R_2$ together are alkylene having 2-3 C atoms, especially ethylene, and in particular compounds of this type in which $R_1$ and $R_2$ are each methyl. Very particularly preferred compounds of the formula III are those in which A has the preferred meaning defined above, $R_1$ and $R_2$ are each methyl and X and Y are each chlorine, or X is bromine and Y is chlorine.

A diastereoisomeric salt of the formula III can be converted directly, in the presence of a base, to an optically active cyclopropanecarboxylic acid derivative of the formula I. Preferably, however, the optically active cyclobutanone of the formula II is obtained from the pure diastereomeric salt of the formula III, by decomposition in the presence of an acid or of a base, and this cyclobutanone is then converted, in the presence of a base, to an optically active cyclopropanecarboxylic acid derivative of the formula I.

The decomposition of the pure diastereomers of the formula III to give an optically active cyclobutanone of the formula II is likewise advantageously carried out in the presence of an inert organic solvent, especially ethanol or acetonitrile, at a temperature of about 30° to 70° C. and preferably in the presence of one mol equivalent of an inorganic or organic proton acid. When the compounds of the formula III are decomposed, the optically active base is also liberated, as well as the cyclobutanone of the formula II. This base can be recovered in very good yield.

Examples of suitable inorganic proton acids are hydrogen halide acids, such as HCl, HBr, HF and HI, nitric acid, phosphoric acid and sulfuric acid. Examples of suitable organic proton acids are: sulfinic acids, such as benzenesulfinic acid; aliphatic and substituted or unsubstituted aromatic sulfonic acids, such as methanesulfonic acid, benzenesulfonic acid, p-toluenesulfonic acid, naphthalenesulfonic acid and naphthalene-1,5-disulfonic acid; aliphatic monocarboxylic acids having preferably 1-18 C atoms, such as formic acid, acetic acid, propionic acid, butyric acid, lauric acid, palmitic acid and stearic acid; halogen-containing monocarboxylic acids, such as chloroacetic acid, dichloroacetic acid, trichloroacetic acid and trifluoroacetic acid; aliphatic dicarboxylic acids having preferably 2-12 C atoms, such as malonic acid, succinic acid, adipic acid and sebacic acid; substituted or unsubstituted aromatic mono- and di-carboxylic acids, such as benzoic acid, toluic acid, naphthoic acid, phthalic acid and terephthalic acid; and aliphatic and aromatic phosphonic and phosphinic acids, such as methyl-, benzyl- or phenyl-phosphonic acid or dimethyl- and diethyl-phosphonic acid or diethyl- and benzene-phosphinic acid.

Hydrochloric acid is preferably used as the proton acid.

Another way in which the optically active cyclobutanone of the formula II can be liberated comprises decomposing the salts of the formula III in the presence of water and an organic solvent, preferably a water-immiscible solvent, such as hydrocarbons, which can be chlorinated, or a dialkyl ether, at a pH value of above 7.0. In order to prevent the Favorski reaction, which takes place at higher pH values, the reaction is preferably carried out a pH values between 7.0 and 7.5 and at temperatures below 25° C. With a particularly mild and time-saving variant of this decomposition procedure, the sulfurous acid liberated during the reaction is oxidised with the aid of a weak oxidising agent, such as an iron-III salt or iodine. The optically active base which is also liberated can be separated from the cyclobutanone by subsequent extraction with an aqueous acid and recovered.

The conversion of the pure diastereomers of the formula III or of the optically active cyclobutanones of the formula II to optically active cyclopropanecarboxylic acid derivatives of the formula I is effected in the presence of a base. Suitable bases are, for example, hydroxides and alcoholates of the formula IV $$M^{n+}(O^-R)_n \qquad (IV)$$

in which M is an alkali metal cation or alkaline earth metal cation and n is the number 1 or 2 and R is as defined under formula I, such as sodium hydroxide, potassium hydroxide, calcium hydroxide and barium hydroxide or sodium methylate, sodium ethylate, sodium isopropylate, sodium sec.-butylate, sodium tert.-butylate and potassium methylate, potassium ethylate, potassium isopropylate, potassium sec.-butylate and potassium tert.-butylate, magnesium methylate or sodium salts and potassium salts of benzyl alcohol, of m-phenoxybenzyl alcohol, of furfuryl alcohol or of 2-thiophenemethanol.

Further suitable bases are alkali metal carbonates and alkaline earth metal carbonates and alkali metal bicarbonates, such as calcium carbonate, barium carbonate, potassium carbonate and sodium carbonate, sodium bicarbonate and potassium bicarbonate. In certain circumstances, the reaction can also be accelerated by the addition of suitable halide acceptors, for example silver nitrate.

The bases are employed in at least the stoichiometric amount, but preferably in excess.

Depending on the nature of the base, the reaction is advantageously carried out in an aqueous, aqueous-organic or organic medium. If the base used is an alkali metal carbonate or alkaline earth metal carbonate, the reaction is carried out in an aqueous or aqueous-organic medium. The reaction in the presence of alkali metal hydroxides or alkaline earth metal hydroxides and alkali metal bicarbonates is also advantageously carried out in an aqueous or aqueous-organic medium. After acidifying the reaction mixture, for example by the addition of concentrated hydrochloric acid, compounds are obtained in which R=H and these can be converted in a known manner to derivatives of the formula I in which R≠H, for example by conversion to the corresponding acid chloride and reaction with an alcohol derived from the radical R.

Suitable organic solvents for the reaction in an aqueous-organic or organic medium are lower alcohols, for example those having not more than 6 C atoms, benzyl alcohol, aliphatic and cyclic ethers, such as diethyl ether, di-n-propyl ether, di-isopropyl ether, tetrahydrofuran, tetrahydropyran and dioxan, and also aliphatic, cycloaliphatic or aromatic hydrocarbons, such as n-pentane, n-hexane, cyclohexane, benzene, toluene and xylenes.

In order to form a cyclopropanecarboxylic acid derivative which has a high content of cis-isomers, the Favorski reaction is advantageously carried out at −10° to +10° C. The reaction mixture is then heated to elevated temperature, and if necessary to the boiling point of the reaction medium, in order to effect complete conversion of the trihalogenoethyl group to a dihalogenovinyl group.

When the pure diastereomers of the formula III are reacted in the presence of a base, opticaly active cyclobutanones of the formula II form as intermediates.

According to a preferred embodiment, the pure diastereomers of the formula III are decomposed, as described, to give optically active cyclobutanones of the formula II, after which the latter are converted in the presence of a base to optically active compounds of the formula I, the products formed being in the main compounds of the formula I in the cis-configuration. If desired, the compounds of the formula I can then be converted to compounds of the formula I'.

The optically active cyclobutanones of the formula II which have the undesired configuration can be converted in the presence of a catalyst to corresponding racemates which contain a high proportion of optically active cyclobutanone with the desired configuration and these racemates can, in turn, be used to obtain diastereomeric sulfonic acid salts of the formula III and thus to obtain optically active cyclobutanones of the formula II which have the desired configuration.

Suitable catalysts for the racemisation of the optically active cyclobutanones of the formula II which have the undesired configuration are acids, quaternary ammonium halides or bases.

Examples of acid catalysts which can be used are inorganic or organic proton acids of the abovementioned type or, alternatively, Lewis acids, such as boron trichloride, boron trifluoride, aluminium trichloride, iron trichloride or zinc chloride.

Furthermore, salts of proton acids, especially hydrogen halide acids, with ammonia or a nitrogen-containing organic base can be employed.

Suitable nitrogen-containing organic bases are aliphatic, cycloaliphatic, araliphatic and aromatic primary, secondary and tertiary amines and also heterocyclic nitrogen bases. Examples are: primary aliphatic amines having not more than 12 C atoms, such as methylamine, ethylamine, n-butylamine, n-octylamine, n-dodecylamine, hexamethylenediamine, cyclohexylamine and benzylamine; secondary aliphatic amines having not more than 12 C atoms, such as dimethylamine, diethylamine, di-n-propylamine, dicyclohexylamine, pyrrolidine, piperidine, piperazine and morpholine; tertiary aliphatic amines, especially trialkylamines having 1-4 C atoms in each alkyl moiety, such as triethylamine, tri-n-butylamine, N-methyl pyrrolidine, N-methylmorpholine, 1,4-diazabicyclo[2.2.2.]-octane and quinuclidine; substituted or unsubstituted primary, secondary and tertiary aromatic amines, such as aniline, toluidine, naphthylamine, N-methylaniline, diphenylamine and N,N-diethylaniline; and also pyridine, picoline, indoline and quinoline.

Preferred salts are those of the formula

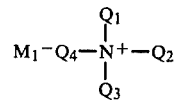

in which $M_1$ is fluorine, bromine or iodine, especially chlorine, $Q_1$, $Q_2$ and $Q_3$ independently of one another are hydrogen or alkyl having 1-18 C atoms and $Q_4$ is hydrogen, alkyl having 1-18 C atoms, cyclohexyl, benzyl, phenyl or naphthyl, and also N-alkyl-pyridinium halides having 1-18 C atoms in the alkyl, especially the corresponding chlorides.

Examples of such salts are: ammonium chloride, ammonium bromide, methylamine hydrochloride, cyclohexylamine hydrochloride, aniline hydrochloride, dimethylamine hydrochloride, di-isobutylamine hydrochloride, triethylamine hydrochloride, triethylamine hydrobromide, tri-n-octylamine hydrochloride, benzyldimethylamine hydrochloride, tetramethyl-, tetraethyl-, tetra-n-propyl- and tetra-n-butyl-ammonium chloride, bromide and iodide, trimethylhexadecylammonium chloride, benzyldimethylhexadecylammonium chloride, benzyldimethyltetradecylammonium chloride, benzyl-trimethyl-, -triethyl- and -tri-n-butyl-ammonium chloride, n-butyl-tri-n-propyl-ammonium bromide, octadecyltrimethylammonium bromide, phenyltrimethylammonium bromide or chloride and hexadecylpyridinium bromide and chloride.

Suitable basic catalysts are organic bases, such as primary, secondary and especially tertiary amines of the formula

in which $Q_5$ is alkyl having 1-8 C atoms, cycloalkyl having 5 or 6 C atoms, benzyl or phenyl and $Q_6$ and $Q_7$ independently of one another are hydrogen or alkyl having 1-8 C atoms, for example triethylamine, tri-n-butylamine, triisopentylamine, tri-n-octylamine, N,N-dimethyl-cyclohexylamine, N,N-dimethyl-benzylamine, N,N-dimethyl-2-ethylhexylamine and N,N-diethylaniline; and also cyclic amines, such as pyridine, quinoline, lutidine, N-alkylmorpholines, such as N-methylmorpholine, N-alkylpiperidines, such as N-methyl- and N-ethyl-piperidine, and N-alkylpyrrolidines, such as N-methyl- and N-ethyl-pyrrolidine; diamines, such as N,N,N',N'-tetramethylethylenediamine, N,N,N',N'-tetramethyl-1,3-diamino-butane and N,N'-dialkylpiperazines, such as N,N'-dimethylpiperazine; bicyclic diamines, such as 1,4-diaza-bicyclo[2.2.2]octane, and bicyclic amidines, such as 1,5-diazabicyclo[5.4.0]-undec-5-ene and 1,5-diazabicyclo[4.3.0]non-5-ene, and finally polymeric basic compounds, such as p-dimethylaminomethyl-polystyrene.

If acids or bases are used in excess, they can also serve as solvents.

Substances which can be used as additional cocatalysts are alkali metal halides, such as potassium iodide, sodium iodide, lithium iodide, potassium bromide, sodium bromide, lithium bromide, potassium chloride, sodium chloride, lithium chloride, potassium fluoride, sodium fluoride and lithium fluoride.

The amount in which the catalyst is employed can vary within wide limits. In general, the catalyst is employed in an amount of about 5 to 100 percent by weight, based on the optically active compound of the formula II.

The racemisation can be carried out either in the melt or in an inert organic solvent. The reaction temperatures for the racemisation in the melt are in general approximately between 50° and 150° C. and in particular between about 80° and 130° C.

Catalysts suitable for the racemisation in the melt are, in particular, the abovementioned salts of hydrogen halide acids with ammonia or organic nitrogen-containing bases, such as trialkylamine hydrochlorides and hydrobromides, having 1–8 C atoms in each alkyl moiety, and very particularly tetraalkylammonium halides, in particular tetraalkylammonium chlorides, bromides and iodides, having 1–18 C atoms in each alkyl moiety. It is also possible to use bases of the type mentioned, especially trialkylamines having 1–8 C atoms in each alkyl moiety, such as triethylamine, tri-n-butylamine and ethyldiisopropylamine.

Suitable inert organic solvents are, for example, those of the type mentioned for the preparation of the salts of the formula III, and also aliphatic monocarboxylic acids. The reaction temperatures for the racemisation in an inert organic solvent are approximately between 0° and 150° C. and especially between about 80° and 130° C. Preferred solvents are acetic acid and ethanol, and the catalysts used are advantageously hydrogen halide acids, especially hydrobromic acid or hydrochloric acid.

In polar solvents, such as aliphatic alcohols or diols, cyclic amides, amides of carbonic acid, amides of phosphorous acid, of phosphoric acid, of phenylphosphonic acid or of aliphatic phosphonic acids, amides of sulfuric acid or of aliphatic or aromatic sulfonic acids, N,N-dialkylamides of aliphatic monocarboxylic acids, nitriles or dialkylsulfoxides of the abovementioned type, the racemisation proceeds on heating, even without the addition of acids, quaternary ammonium halides or bases. In these cases, the solvent acts as the catalyst.

Cyclobutanones of the formula II in which $R_1$ and $R_2$ are as defined and X and Y independently of one another are chlorine or bromine can be prepared, starting from readily accessible starting materials, in a simple manner and in good yield by a novel synthesis which comprises reacting a compound of the formula V

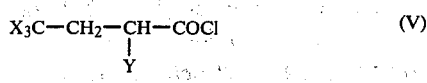  (V)

in the presence of an organic base, with an olefin of the formula VI

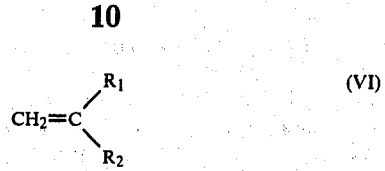

to give a compound of the formula VII

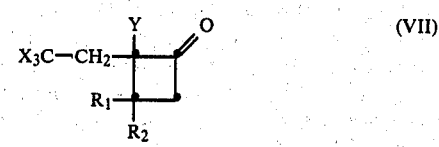

and rearranging the compound of the formula VII in the presence of a catalyst to give a cyclobutanone of the formula II in which $R_1$, $R_2$, Y and X are as defined (cf. German Offenlegungsschrift No. 2,813,337).

Cyclobutanones of the formula II in which X, $R_1$ and $R_2$ are as defined under formula I or I' and Y is a group $-OSO_2R'$ can be obtained by converting a compound of the formula VII, in the presence of an inorganic base, such as alkali metal hydroxides, carbonates or bicarbonates or alkaline earth metal hydroxides, carbonates or bicarbonates, to a 2,2,2-trichloro- or 2,2,2-tribromoethylhydroxycyclobutanone of the formula VIIIa or VIIIb

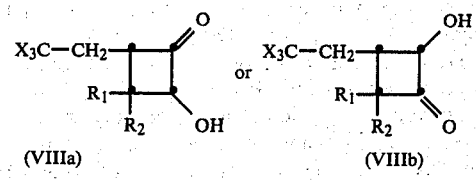

(VIIIa)                (VIIIb)

and then reacting the compound of the formula VIIIa or VIIIb, in the presence of an organic base, such as tertiary amines, with a compound $R'—SO_2—Cl$. This procedure in general yields mixtures of cyclobutanones of the formula II in which $Y=-OSO_2R'$ and isomers of the formula

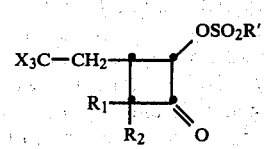

which can be separated from one another in a conventional manner.

Preferred compounds of the formula I or I' are those in which R is an alkyl group having 1–4 carbon atoms and in particular hydrogen.

Alkyl groups R can be straight-chain or branched. Examples of suitable alkyl groups R are: the methyl, ethyl, n-propyl, isopropyl and n-butyl group. Preferably, the said alkyl groups are straight-chain.

Alkyl groups R' can likewise be straight-chain or branched and preferably have 1–4 C atoms. Halogenoalkyl groups R' are in particular chlorinated, brominated or fluorinated, branched or straight-chain alkyl groups. Examples of suitable halogenoalkyl groups R' are: the chloromethyl, trifluoromethyl or perfluoro-n-butyl group.

Possible substituents in a substituted phenyl group R' are, in particular, alkyl groups having 1–4 and especially 1 or 2 C atoms, halogen atoms, such as chlorine and bromine, and nitro groups. Preferably, phenyl groups R' have only one substituent of the indicated type. Examples of suitable substituted phenyl groups R' are: the 3- or 4-methylphenyl, 4-ethylphenyl, 2- and 4-nitrophenyl, 4-chlorophenyl and 4-bromophenyl group.

If R' is a naphthyl group, the sulfonyl group can be in the 1-position or 2-position of the naphthalene radical.

Compounds of the formula I or I' in which R=H or alkyl having 1-4 C atoms, which have been obtained according to the invention, can be converted in a manner known per se to compounds of the formula I or I' in which R is a group

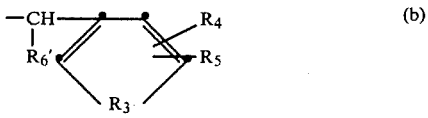
(b)

$R_3$, $R_4$ and $R_5$ are as defined under formula I or I' and $R_6'$ is hydrogen, ethynyl or cyano, for example by reaction with corresponding halides or alcohols (the latter if desired with prior conversion of the compound of the formula I or I' to the acid chloride) or by trans-esterification.

The bromination of the compounds of the formula I to give compounds of the formula I' can be carried out by methods known per se, for example by the method described in German Offenlegungsschrift No. 2,805,312, before or after any conversion of compounds of the formula I in which R=H or alkyl to compounds of the formula I in which R is a group (a) or (b).

Preferred cyclobutanones of the formula II are those in which X is chlorine or bromine, one of $R_1$ and $R_2$ is methyl and the other is hydrogen or methyl, or $R_1$ and $R_2$ together are alkylene having 2-3 C atoms, especially ethylene, and Y is chlorine, bromine or a group —O—SO$_2$R', in which R' is alkyl or halogenoalkyl having 1-4 C atoms, benzyl, phenyl, methylphenyl, nitrophenyl, chlorophenyl or bromophenyl, and in particular compounds of the formula II and III in which A has the preferred meaning defined above and X is chlorine, $R_1$ and $R_2$ are each methyl and Y is a group —OSO$_2$R', in which R' is methyl, 4-methylphenyl or 4-bromophenyl.

Particularly preferred cyclobutanones of the formula II are those in which X and Y independently of one another are chlorine or bromine, one of $R_1$ and $R_2$ is methyl and the other is hydrogen or methyl, or $R_1$ and $R_2$ together are alkylene having 2-3 C atoms, especially ethylene, and in particular compounds of this type in which $R_1$ and $R_2$ are each methyl. Very particularly preferred cyclobutanones of the formula II are those in which $R_1$ and $R_2$ are each methyl and X and Y are each chlorine, or X is bromine and Y is chlorine.

The compounds of the formula I and I' in which R is a group

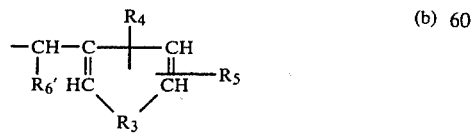
(b)

and $R_3$, $R_4$, $R_5$ and $R_6'$ are as defined are suitable for the control of diverse animal or plant pests, especially insects. The properties, fields of application and use forms of these active substances are described in the literature (cf., for example, Nature, 246, 169–170 (1973); Nature, 248, 710–711 (1974); Proceedings 7th British Insecticide and Fungicide Conference, 721–728 (1973); Proceedings 8th British Insecticide and Fungicide Conference, 373–78 (1975); J. Agr. Food Chem. 23, 115 (1973); U.S. Pat. No. 3,961,070 and German Offenlegungsschrift Nos. 2,553,991, 2,439,177, 2,326,077 and 2,614,648).

The process according to the invention enables optically active cyclopropanecarboxylic acid derivatives of the formula I or I' with the cis-configuration to be prepared in a simple manner. This is of particular interest, since the cyclopropanecarboxylic acid derivatives of the formula I or I', in which R is a group (b), possess a considerably more powerful insecticidal action than the corresponding compounds with the trans-configuration.

A particular advantage of the process according to the invention is that the optically active cyclobutanones of the formula II which are thus obtained with the undesired configuration can be converted again, in the presence of catalysts, to the starting racemate with high proportions of the cis-configuration.

The process according to the invention is illustrated in more detail by the following examples.

EXAMPLE 1

The salt of 2-chloro-3,3-dimethyl-1-hydroxy-4-(2',2',2'-trichloroethyl)-cyclobutane-1-sulfonic acid with (−)- or (+)-1-phenylethylamine (a) Sulfur dioxide is passed for 90 minutes into a solution of 105.6 g (0.4 mol) of racemic 2-chloro-3,3-dimethyl-4-(2',2',2'-trichloroethyl)-cyclobutan-1-one and 48.5 g (0.4 mol) of (−)-1-phenylethylamine in 2 liters of acetonitrile and 40 ml of water, at room temperature (20°–25° C.), with stirring. The reaction mixture, which according to monitoring by thin layer chromatography contains no further starting materials, is then filtered and the reaction product, which is a white powder, is subjected to suction until dry; yield: 203.1 g. (>100% of theory). The crude product is then dissolved in five times the amount (ml/g) of ethanol/water in a ratio by volume of 1:1, at 60°–70° C. The product obtained after cooling is filtered off and subjected to suction until dry. This crystallisation procedure is carried out a total of 4 times; yield: 60.6 g of fine white needles; melting point 136°–138° C. (decomposition). Further product can be obtained by working up the mother liquors.

(b) In an analogous manner, 26.4 g (0.1 mol) of racemic 2-chloro-3,3-dimethyl-4-(2',2',2'-trichloroethyl)-cyclobutan-1-one are reacted with 12.1 g of (+)-1-phenylethylamine in 500 ml of acetonitrile and 10 ml of water, with sulfur dioxide. The crude product is recrystallised analogously to (1a); melting point 134°–138° C. (decomposition).

The racemic 2-chloro-3,3-dimethyl-4-(2',2',2'-trichloroethyl)-cyclobutan-1-one used as the starting material can be prepared according to German Offenlegungsschrift No. 2,813,337.

EXAMPLE 2

(+)-2-Chloro-3,3-dimethyl-4-(2',2',2'-trichloroethyl)-cyclobutan-1-one.

(a) 5.0 g of the salt obtained according to Example (1a) are suspended in a solution of 60 ml of ethanol and 25 ml of 6 N hydrochloric acid. The suspension is stirred for 1 hour at 60° C. and allowed to cool and is then concentrated to about ⅓ its volume in a rotary evaporator. The residue is diluted with water and the cyclobutanone which precipitates is taken up in diethyl ether. After drying the organic extract over sodium sulfate, the extract is evaporated. On leaving to stand, 2.6 g (92% of theory) of the cyclobutanone crystallise out; this product has the following specific rotations: $[\alpha]_{365}^{20} = +104°$, $[\alpha]_{436}^{20} = +22°$, $[\alpha]_{546}^{20} = +4°$, $[\alpha]_{578}^{20} = +2°$, $[\alpha]_{589}^{20} = +2°$ ($CCl_4$, 0.85%).

(b) A suspension of 10.7 g of the salt obtained according to Example (1a) in 120 ml of water is covered with a layer of ether and the mixture is rendered weakly alkaline (pH 8–9) by adding aqueous sodium bicarbonate solution, with intensive stirring. After separating off the ether phase, the aqueous phase is extracted several times more with ether. The combined extracts are washed, first with 6 N hydrochloric acid and then with water, and dried over magnesium sulfate. After evaporating off the ether and crystallising the residue, 4.9 g of (+)-2-chloro-3,3-dimethyl-4-(2′,2′,2′-trichloroethyl)-cyclobutan-1-one with a specific rotation $[\alpha]_{365}^{20} = +105°$ ($CCl_4$, 0.82%) are obtained.

2.55 g of (−)-1-phenylethylamine are obtained from the wash water containing hydrochloric acid, by adding sodium hydroxide solution and extracting with ether.

EXAMPLE 3

(+)-cis-2-(2′,2′-Dichlorovinyl)-3,3-dimethylcyclopropane-1-carboxylic acid (a) 2.2 g (8.3 mmols) of the (+)-cyclobutanone obtained according to Example (2) are stirred together with 10 ml of 2.5 N sodium hydroxide solution for 8 hours at 0° C. and overnight at room temperature. The reaction solution, which according to the NMR spectrum contains a mixture of cis- and trans-2-(2′,2′,2′-trichloroethyl)-3,3-dimethylcyclopropane-1-carboxylic acid in a ratio of about 80:20, is then refluxed for 2½ hours. After cooling, the solution is acidified, the product is taken up in diethyl ether and the extracts are dried over sodium sulfate. On evaporation, 1.5 g (86% of theory) of 2-(2′,2′-dichlorovinyl)-3,3-dimethyl-cyclopropane-1-carboxylic acid are obtained in the form of an 83:17 cis/trans mixture. The (+)-cis-acid is separated off in the pure form from this mixture by chromatography on silica gel. Specific rotation: $[\alpha]_D^{20} = +29°$ ($CHCl_3$ 1.1%).

(b) 4.9 g (105 mmols) of the salt obtained according to Example (1b) are added to 42 ml of 1.25 N sodium hydroxide solution which has been cooled to 0° C., and the suspension is stirred for 2 hours at 0° C. The reaction solution, which according to the NMR spectrum contains a mixture of cis- and trans-2-(2′,2′,2′-trichloroethyl)-3,3-dimethylcyclopropane-1-carboxylic acid in a ratio of about 55:45, is then refluxed for 3 hours. After cooling, the reaction solution is extracted several times with diethyl ether, the (+)-1-phenylethylamine employed being recovered. The alkaline aqueous phase is then acidified with dilute sulfuric acid and the reaction product is taken up in diethyl ether. After drying the extract over sodium sulfate, it is concentrated. 2.0 g (91% of the theory) of 2-(2′,2′-dichlorovinyl)-3,3-dimethylcyclopropane-1-carboxylic acid are obtained in the form of an approximately 60:40 cis/trans mixture. By chromatography of this mixture on silica gel (eluant hexane/diethyl ether in a ratio by volume of 1:1), the (−)-cis-acid is first separated off; $[\alpha]_D^{20} = -29°$ ($CHCl_3$, 1.3%).

The subsequent fractions yield the (+)-trans-acid, which is obtained in the pure form by recrystallisation from n-hexane; $[\alpha]_D^{20} = +34°$ ($CHCl_3$, 1.3%).

EXAMPLE 4

The salt of 2-chloro-3,3-dimethyl-1-hydroxy-4-(2′,2′,2′-tribromoethyl)-cyclobutane-1-sulfonic acid with (−)-1-phenylethylamine Sulfur dioxide is passed for 1 hour into a solution of 21.0 g (53 mmols) of racemic 2-chloro-3,3-dimethyl-4-(2′,2′,2′-tribromoethyl)-cyclobutan-1-one and 6.4 g (53 mmols) of (−)-1-phenylethylamine in 270 ml of acetonitrile and 6 ml of water, with stirring, at a temperature of below 30° C., and the mixture is then stirred for a further 1½ hours at room temperature. The crystals which have formed are filtered off and subjected to suction until dry. The product is then recrystallised in a manner analogous to that described in Example (1a). Yield: 8.9 g of fine white needles; melting point 126°–128° (decomposition). Further material can be obtained from the mother liquors.

The racemic 2-chloro-3,3-dimethyl-4-(2′,2′,2′-tribromoethyl)-cyclobutan-1-one used as the starting material can be prepared as follows:

324.8 g (1.0 mol) of 4,4,4-tribromobutyric acid are warmed with 600 g of thionyl chloride and 1 ml of dimethylformamide, first for 2 hours at 40° C. and then for 3 hours at 75° C. The excess thionyl chloride is then distilled off and the residue is rectified under a high vacuum. 326.0 g (95% of theory) of 4,4,4-tribromobutyric acid chloride with a boiling point of 71° to 73° C./0.05 mm Hg are obtained.

343.2 g (1.0 mol) of 4,4,4-tribromobutyric acid chloride are dissolved in 600 g of thionyl chloride, and 266.0 g (2.0 mols) of N-chlorosuccinimide are added in portions at 60° C., whilst at the same time exposing the mixture to a high-pressure mercury lamp. After all of the N-chlorosuccinimide has been added, the resulting mixture is stirred for 5 hours at 60° C., with exposure to the said lamp. The thionyl chloride is then distilled off and the residue is rectified under a high vacuum. 309.7 g (82% of theory) of 2-chloro-4,4,4-tribromobutyric acid chloride with a boiling point of 59° to 63° C./0.05 mm Hg are obtained.

90.6 g (0.24 mol) of 2-chloro-4,4,4-tribromobutyric acid chloride in 360 ml of cyclohexane are initially introduced into an autoclave and 134 g (2.4 mols) of isobutylene are injected. A solution of 24.2 g (0.24 mol) of triethylamine in 120 ml of cyclohexane is then pumped in at 65° C., in the course of 4 hours. After all of the triethylamine solution has been added, the reaction mixture is kept at 65° C. for a further 3 hours. The triethylamine hydrochloride which has formed is then filtered off and the solvent is distilled off. The residue is dissolved in a solvent mixture consisting of equal parts of toluene and hexane and the solution is filtered through silica gel. 51.4 g (54% of theory) of 2-chloro-3,3-dimethyl-2-(2′,2′,2′-tribromoethyl)-cyclobutan-1-one with a melting point of 95° to 97° C. are obtained from the filtrate after evaporating off the solvent.

22.8 g (0.054 mol) of 2-chloro-3,3-dimethyl-2-(2′,2′,2′-tribromoethyl)-cyclobutan-1-one are dissolved in 220 ml of absolute ethanol after the latter has been saturated with hydrogen chloride. The resulting solution is stirred for 5 hours at 80° C. The reaction mixture is then concentrated to about ⅓ the initial volume in a rotary evaporator, water is added to the residue and the mixture is extracted with ether. The ether extract is washed, first with saturated sodium chloride solution and then with sodium bicarbonate solution, and dried over sodium sulfate. The residue obtained after evaporating off the ether is chromatographed on silica gel, toluene being used as the eluant. After combining and evaporating the pure fractions, 17.1 g (75% of theory) of 2-chloro-3,3-dimethyl-4-(2',2',2'-tribromoethyl)-cyclobutan-1-one with a melting point of 87° to 89° C. are obtained.

EXAMPLE 5

(+)-2-Chloro-3,3-dimethyl-4-(2',2',2'-tribromoethyl)-cyclobutan-1-one (a) 2.0 g (87% of theory) of (+)-cyclobutanone are liberated in the manner described in Example 2 from 3.5 g (5.8 mmols) of the salt obtained according to Example 4. This cyclobutanone has the following specific rotations: $[\alpha]^{20}_{365} = +72°$, $[\alpha]^{20}_{436} = +29°$, $[\alpha]^{20}_{546} = +13°$, $[\alpha]^{20}_{578} = +11°$, $[\alpha]^{20}_D = +10°$.

(b) 50 ml of saturated sodium bicarbonate solution are added to a suspension of 10.6 g of the salt obtained according to Example 4 in 250 ml of water and the mixture is covered with a layer of ether. An iodine solution prepared by dissolving 20 g of iodine in 100 ml of ethanol is then added dropwise, with intensive stirring, until the coloration is just permanent (consumption: about 20 ml). The ether phase is separated off, washed, first with hydrochloric acid, then with sodium thiosulfate solution and then with sodium chloride solution, and dried over sodium sulfate. After evaporating off the ether and crystallising the residue from hexane/ether, 6.2 g of (+)-2-chloro-3,3-dimethyl-4-(2',2',2'-tribromoethyl)-cyclobutan-1-one are obtained.

EXAMPLE 6

1.6 g (4 mmols) of the cyclobutanone obtained according to Example 5) are stirred together with 11 ml of 1.25 N sodium hydroxide solution for 22 hours at 0° C. The reaction solution, which according to the NMR spectrum contains a mixture of cis- and trans-2-(2',2',2'-tribromoethyl)-3,3-dimethyl-cyclopropane-1-carboxylic acid in a ratio of about 80:20, is then stirred for 1 hour at 80° C. The subsequent procedure is as described in Example 3. 1.0 g (84%) of 2-(2',2'-dibromovinyl)-3,3-dimethyl-cyclopropane-1-carboxylic acid is obtained in the form of an 80:20 cis/trans mixture. The (+)-cis-acid is obtained in the pure form by chromatography on silica gel; $[\alpha]^{20}_D = +18°$, melting point 127°–129° C.

EXAMPLE 7

(a) 114.2 mg of (−)-2-chloro-3,3-dimethyl-4-(2',2',2'-trichloroethyl)-cyclobutan-1-one are dissolved at room temperature in 6 ml of acetic acid which contains 16.5% by weight of hydrobromic acid. On standing for 20 hours, the specific rotation of the solution goes back from the value observed initially, that is to say $[\alpha]^{20}_{546} = -19.3°$, to $[\alpha]^{20}_{546} = -0.6°$. For working up, the solution is poured into water, the resulting mixture is extracted several times with n-pentane and the pentane extracts are washed with dilute ice-cold sodium bicarbonate solution and dried over sodium sulfate. Evaporation of the solution yields 110 mg of the racemic cyclobutanone, which according to the NMR spectrum is in the form of a 95:5 cis/trans mixture.

(b) 264 mg (1 mmol) of (−)-2-chloro-3,3-dimethyl-4-(2', 2',2'-trichloroethyl)-cyclobutan-1-one with a specific rotation of $[\alpha]^{20}_{365} = -70°$ (CCl$_4$) are stirred together with 28 mg (0.1 mmol) of tetra-n-butylammonium chloride for 4 hours at 120° C. After cooling, diethyl ether and water are added to the reaction product. The ether phase is washed with water, dried over sodium sulfate and filtered through a little silica gel. Evaporation of the filtrate yields 258 mg of the racemic cyclobutanone, which according to the NMR spectrum is in the form of a 90:10 cis/trans mixture.

EXAMPLE 8

Resolution of 2-chloro-3,3-dimethyl-4-(2',2',2'-trichloroethyl)-cyclobutan-1-one into the two optical antipodes (a) 24 g of SO$_2$ are passed into a solution of 10 g of 2-chloro-3,3-dimethyl-4-(2',2',2'-trichloroethyl)-cyclobutan-1-one, 190 ml of acetonitrile and 3.7 ml of water, with vigorous stirring. 6.2 g of (+)-ephedrine, dissolved in 30 ml of acetonitrile, are now added to the solution at 20° C., the reaction mixture is stirred for one hour and filtered and the material on the filter is washed with a little diethyl ether. The salt obtained is recrystallised twice from, in each case, 45 ml of 50% aqueous ethanol, and is then decomposed with hydrochloric acid, and 2-chloro-3,3-dimethyl-4-(2',2',2'-trichloroethyl)-cyclobutan-1-one with a specific rotation of $[\alpha]_{365} = +105°$ (c=1.5, CCl$_4$) is obtained.

(b) Optically active 2-chloro-3,3-dimethyl-4-(2',2',2'-trichloroethyl)-cyclobutan-1-one of $[\alpha]_{365} = +107°$ (c=0.9, CCl$_4$) can be prepared in a manner analogous to that described under (a), using L-(+)-threo-2-dimethylamino-1-(p-nitrophenyl)-1,3-propanediol.

EXAMPLE 9

Preparation of (R)-and (S)-α-cyano-3-phenoxy-benzyl (1R-cis)-2-(2',2'-dichlorovinyl)-3,3-dimethyl-cyclopropane-1-carboxylate (isomer A and isomer B)

19.6 g of oxalyl chloride, 16 g of (1R-cis)-2-(2',2'-dichlorovinyl)-3,3-dimethyl-cyclopropane-1-carboxylic acid, dissolved in 100 ml of CH$_2$Cl$_2$, 37.2 g of pyridine, dissolved in 50 ml of CH$_2$Cl$_2$, and 17 g of (R,S)-α-cyano-3-phenoxybenzyl alcohol, dissolved in 100 ml of CH$_2$Cl$_2$, are added dropwise successively, at −20° C., to a solution of 1,000 ml of methylene chloride and 33.5 g of N,N-dimethylformamide. The reaction mixture is allowed to warm slowly to room temperature and is stirred for 16 hours at 20° C. and evaporated to dryness under reduced pressure, n-hexane is added to the residue and the organic phase is washed with 1 N hydrochloric acid, saturated sodium bicarbonate solution and sodium chloride solution and dried over MgSO$_4$ and the solvent is distilled off under reduced pressure. This yields 30 g of a 1:1 mixture of isomers A and B. Chromatography on silica gel using a mixture of petroleum ether/diisopropyl ether as the eluant yields first pure (R)-α-cyano-3-phenoxybenzyl (1R-cis)-2-(2',2'-dichlorovinyl)-3,3-dimethyl-cyclopropane-1-carboxylate (isomer A) and then (S)-α-cyano-3-phenoxy-benzyl (1R-cis)-2-(2',2'-dichlorovinyl)-3,3-dimethyl-cyclopropane-1-carboxylate (isomer B).

Isomer A: $[\alpha]_D = -32°$ (c=1.1%, benzene).
$n^{21}_D = 1.5665$;
Isomer B: $[\alpha]_D = +67°$ (c=1.2%, benzene).
Melting point = 55°–56° C.

EXAMPLE 10

(S)-α-Cyano-3-phenoxybenzyl (1R-cis)-2-(2',2'-dichloro-(S or R)-1',2'-dibromoethyl)-3,3-dimethyl-cyclopropane-1-carboxylate (isomer 1 and isomer 2 respectively).

2 g of (S)-α-cyano-3-phenoxybenzyl (1R-cis)-2-(2',2'-dichlorovinyl)-3,3-dimethyl-cyclopropane-1-carboxylate are dissolved in 30 ml of CCl$_4$, and a solution of 0.78 g of bromine in 5 ml of CCl$_4$ is then added in portions. During the addition of the bromine, the reaction vessel is irradiated with a 6 watt daylight lamp. After 30 minutes, the reaction solution is concentrated to dryness under reduced pressure. The crude product is subjected to chromatography on silica gel and, using a mixture of n-hexane and diisopropyl ether (10:1), first isomer 1 with $n^{21}_D = 1.5791$ and then isomer 2 with $n^{21}_D = 1.5782$ are eluted.

EXAMPLE 11

Racemisation of (+)-2-chloro-3,3-dimethyl-4-(2',2',2'-tribromoethyl)-cyclobutan-1-one.

4.0 g of (+)-2-chloro-3,3-dimethyl-4-(2',2',2'-tribromoethyl)-cyclobutan-1-one ([α]$^{20}_{365}$=70°) and 0.45 g of tetrabutylammonium chloride are stirred at 110° C. for 4 hours. The cooled melt is digested with ether. The ether phase, which has been separated off, is washed with water and filtered through a little silica gel. After evaporating off the ether, this yields 3.75 g of racemic 2-chloro-3,3-dimethyl-4-(2',2',2'-tribromoethyl)-cyclobutan-1-one, which according to the NMR spectrum is in the form of a 95:5 cis/trans mixture.

After recrystallisation from hexane/ether, 3.05 g of racemic cis-2-chloro-3,3-dimethyl-4-(2',2',2'-tribromoethyl)-cyclobutan-1-one with a melting point of 88°–89° C. are obtained.

EXAMPLE 12

(a) Preparation of (R,S)-α-cyano-3-(4-fluorophenoxy)-benzyl (1R-cis)-2-(2',2'-dichlorovinyl)-3,3-dimethyl-cyclopropane-1-carboxylate (isomer A and isomer B).

First 31.2 g of pyridine and then a solution of 72.3 g of (R,S)-α-cyano-3-(4-fluorophenoxy)-benzyl alcohol in 200 ml of toluene are added dropwise to a solution of 67.7 g of (1R-cis)-2-(2',2'-dichlorovinyl)-2,2-dimethyl-cyclopropane-1-carboxylic acid chloride in 500 ml of toluene, at 0°–5° C., with stirring. The cooling bath is then removed and the mixture is stirred for a further 16 hours at room temperature. The reaction mixture is then diluted to 1,000 ml by adding water and the phases are separated. The organic phase is washed, first twice with, in each case, 500 ml of 2 N hydrochloric acid and then successively with 1,000 ml of 10% potassium carbonate solution and 1,000 ml of saturated sodium bicarbonate solution and three times with 1,000 ml of sodium chloride solution, and dried over magnesium sulfate. By evaporating off the solvent under reduced pressure and filtering the resulting crude product through silica gel with a mixture of 1 part of ether and 10 parts of hexane, a 1:1 mixture of (R)-α-cyano-3-(4-fluorophenoxy)-benzyl (1R-cis)-2-(2',2'-dichlorovinyl)-3,3-dimethylcyclopropane-1-carboxylate (isomer A) and (S)-α-cyano-3-(4-fluorophenoxy)-benzyl (1R-cis)-2-(2',2'-dichlorovinyl)-3,3-dimethylcyclopropane-1-carboxylate (isomer B) with a refractive index of $n^{20}_D = 1.5531$ is obtained.

The mixture of isomers A and B is resolved by chromatography on a silica gel column using a mixture of 85 parts of petroleum ether and 15 parts of diisopropyl ether as the solvent system. First isomer A and then isomer B is obtained. The following specific rotations and refractive indices were measured for the two isomers:

Isomer A: [α]$_D$ = −34°±1° (c=1.291; benzene)
[α]$_D$ = −22°±1° (c=1.407; chloroform)
$n^{21}_D = 1.5580$ Isomer B: [α]$_D$ = +67°±1° (c=1.277; benzene)
[α]$_D$ = +30°±1° (c=1.069; chloroform)
Melting point: 59°–60° C.

Isomer B can also be separated from the resulting mixture of isomers A and B as follows:

A solution of 11 g of the mixture of isomers A and B and 1.28 g of triethylamine in 43 ml of isopropanol is stirred for 24 hours at 0° C. The white precipitate thus formed is filtered off and washed with 5 ml of ice-cold isopropanol. This yields isomer B with a melting point of 59°–60° C. The specific rotations measured in benzene and chloroform are identical to the specific rotations of the isomer B separated off by chromatography.

(b) Preparation of (S)-α-cyano-3-(4-fluorophenoxy)-benzyl (1R-cis)-2-(1',2'-dibromo-2',2'-dichloroethyl)-3,3-dimethyl-cyclopropane-1-carboxylate A solution of 8.2 g of bromine in 10 ml of carbon tetrachloride is added dropwise, at 60° C., to a solution of 22.4 g of isomer B and 41 mg of α,α'-azoisobutyronitrile in 150 ml of carbon tetrachloride. After all of the bromine solution has been added, the reaction mixture is refluxed for 2½ hours. The solvent is then distilled off under reduced pressure. The resulting crude product is subjected to chromatography on silica gel, using a mixture of 95 parts of hexane and 5 parts of tetrahydrofuran. This yields (S)-α-cyano-3-(4-fluorophenoxy)-benzyl (1R-cis)-2-(1',2'-dibromo-2',2'-dichloroethyl)-3,3-dimethylcyclopropane-1-carboxylate with a refractive index $n^{30}_D = 1.5680$ and a specific rotation of [α]$^{20}_D$ = +38°±1° (c=0.756; benzene) [α]$^{20}_D$ = +21°±1° (c=1.066; chloroform).

What is claimed is:

1. A compound of the formula [III]

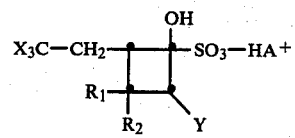

in which X is chlorine or bromine; one of R$_1$ and R$_2$ is methyl and the other is hydrogen or methyl, or R$_1$ and R$_2$ together are alkylene having 2–4 C atoms; A is an optically active base selected from the group consisting of S(+)-2-amino-1-butanol, R(−)-2-aminobutanol, L(+)-threo-2-amino-1-phenyl-1,3-propanediol, (−)-brucine, (+)-quinidine, (−)-quinine, (−)-cinchonidine, (+)-cinchonine, (+)-dehydroabietylamine, (+)-yohimbine, (−)-nicotine, (−)-ephedrine, (+)-ephedrine, (−)-N-methyl-ephedrine, R(+)-1-naphthyl-1-ethylamine, S(−)-1-naphthyl-1-ethylamine, S(−)-1-phenylethylamine, R(+)-1-phenylethylamine, (+)-pseudoephedrine, (−)-α-phenyl-β-p-tolylethylamine and (−)-and (+)-threo-1-(p-nitrophenyl)-2-N,N-dimethylaminopropane-1,3-diol; and Y is chlorine, bromine or a group —OSO$_2$R', in which R' is alkyl having 1–4 C atoms, halogenalkyl having 1–4 C atoms, benzyl, naphthyl phenyl, methylphenyl, ethylphenyl, nitrophenyl, chlorophenyl or bromophenyl.

2. A compound according to claim 1, in which A is R(−)-2-amino-1-butanol, (−)-ephedrine, (+)-ephedrine, S(−)-1-phenylethylamine or R(+)-1-phenylethylamine; X and Y independently of one another are chlorine or bromine; and one of $R_1$ and $R_2$ is methyl and the other is hydrogen or methyl, or $R_1$ and $R_2$ together are alkylene having 2–3 C atoms.

3. A compound according to claim 1, in which X and Y are each chlorine, or X is bromine and Y is chlorine; and $R_1$ and $R_2$ are each methyl.

* * * * *